United States Patent [19]

Peers-Trevarton

[11] Patent Number: 4,574,800

[45] Date of Patent: Mar. 11, 1986

[54] IMPLANTED LEAD EXTRACTOR

[75] Inventor: Charles A. Peers-Trevarton, Coral Springs, Fla.

[73] Assignee: Cordis Corporation, Miami, Fla.

[21] Appl. No.: 679,566

[22] Filed: Dec. 7, 1984

[51] Int. Cl.⁴ .............................................. A61B 17/50
[52] U.S. Cl. .............................. 128/303 R; 128/419 P; 128/785
[58] Field of Search .................. 128/303 R, 328, 343, 128/345, 419 P, 784–786; 604/104–107

[56] References Cited

U.S. PATENT DOCUMENTS

| | | | |
|---|---|---|---|
| 862,712 | 8/1907 | Collins | 128/345 |
| 1,878,671 | 9/1932 | Cantor | 128/343 |
| 2,201,749 | 5/1940 | Vandegrift | 604/107 |
| 2,689,568 | 9/1954 | Wakefield | 128/345 |
| 3,154,079 | 10/1964 | McKay | 604/175 |
| 4,471,777 | 9/1984 | McCorkle, Jr. | 128/303 R |
| 4,498,482 | 2/1985 | Williams | 128/786 |

Primary Examiner—William E. Kamm
Assistant Examiner—Mitchell J. Shein
Attorney, Agent, or Firm—Lockwood, Alex, Fitzgibbon & Cummings

[57] ABSTRACT

An extractor is provided for safely and easily removing an implanted lead such as a cardiac pacing lead from a patient. The extractor accomplishes a method that includes imparting a wedging condition to an implanted lead at a distal location thereof, such as a location at or near an electrode implanted in an atrium or ventricle of a heart, which wedging condition permits a pulling force to be transmitted along the length of the extractor and to the implanted electrode location, thereby avoiding the need to impart any substantial pulling forces along length of the lead itself. The extractor includes a tube and a line which move with respect to each other to impart the wedging condition onto a distal portion of the implanted lead.

17 Claims, 6 Drawing Figures

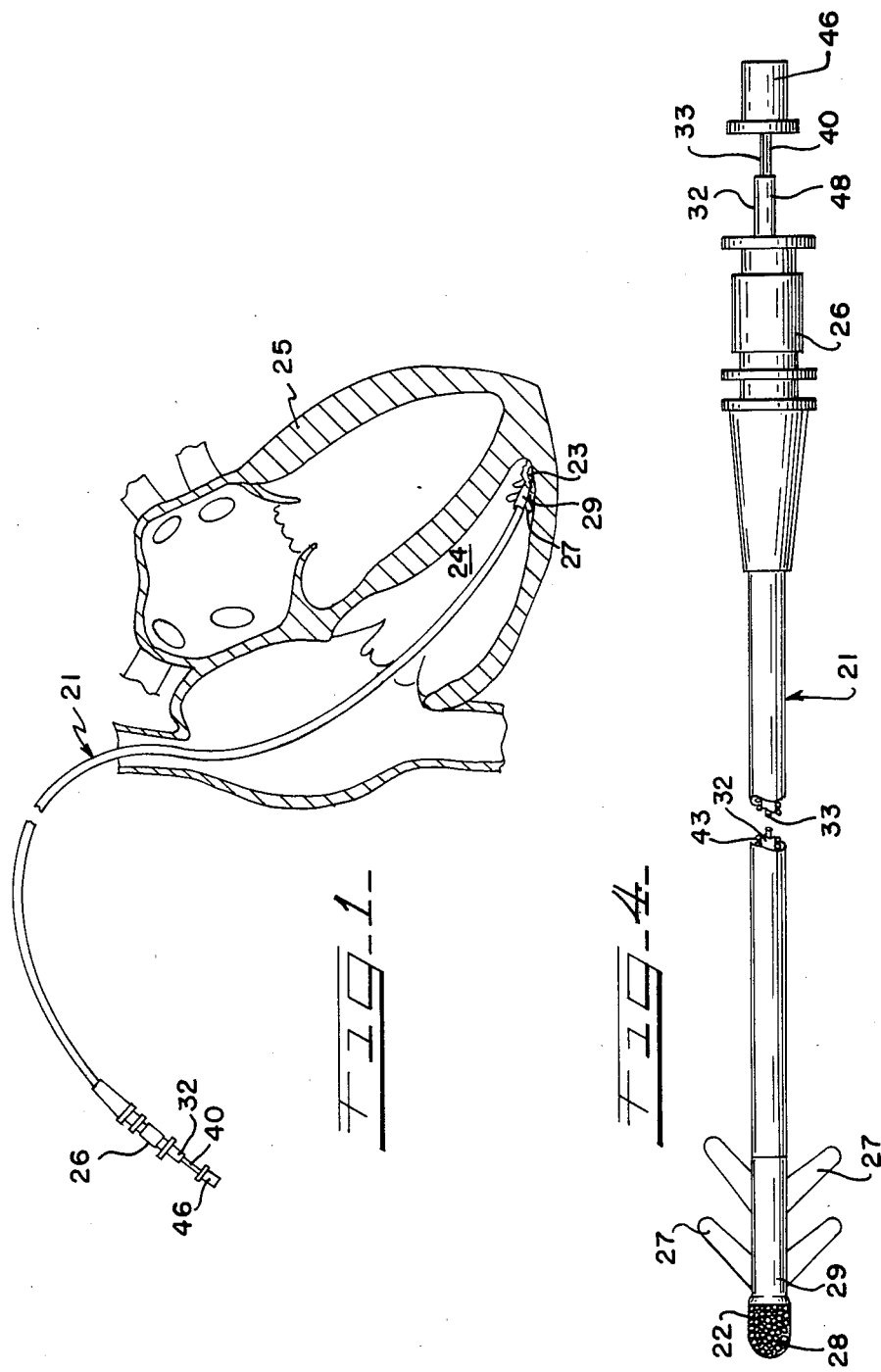

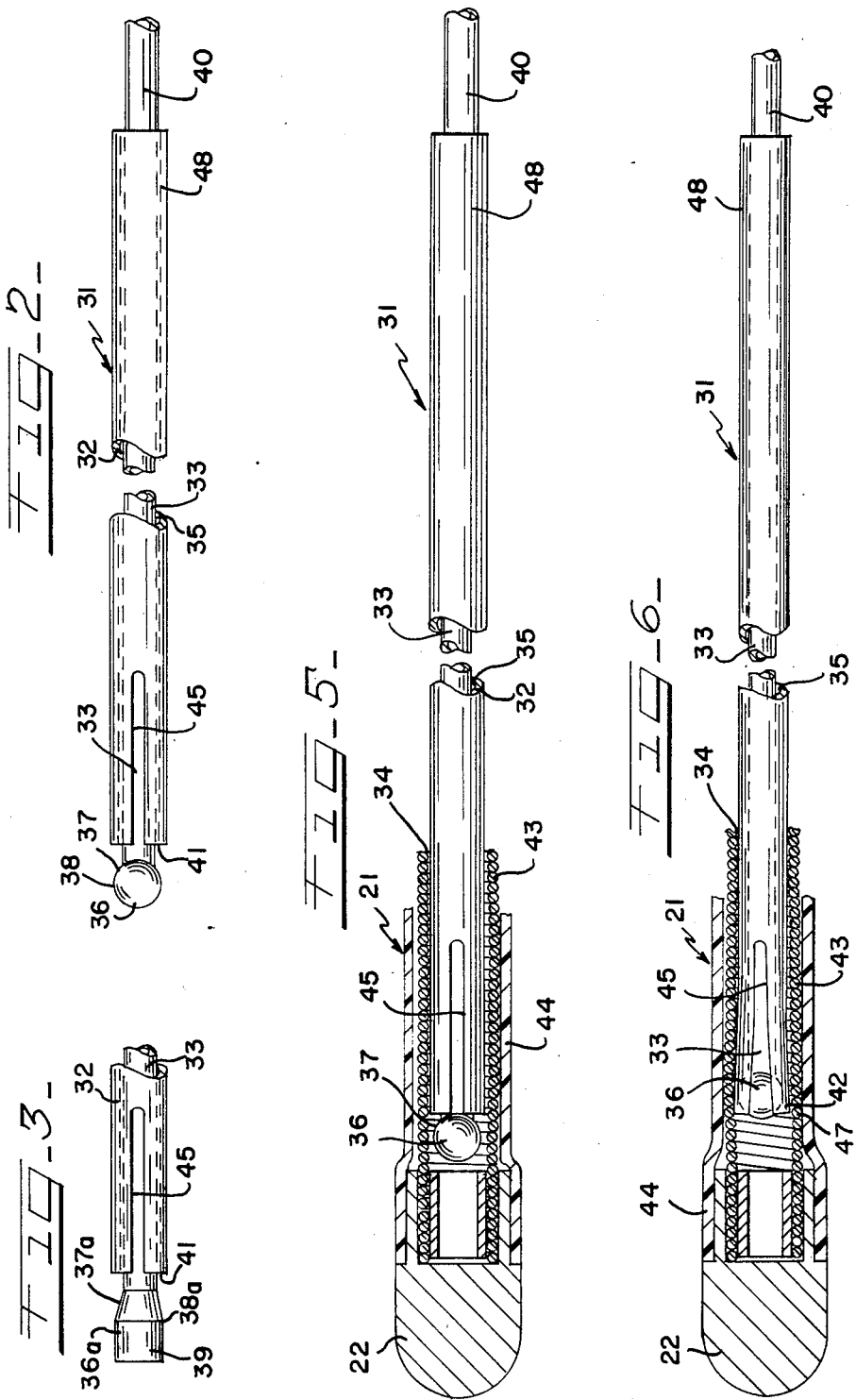

IMPLANTED LEAD EXTRACTOR

DESCRIPTION

This invention generally relates to extracting implanted leads, particularly removing entire cardiac pacing leads including those having remotely located implanted electrodes that have become generally overgrown with tissue. A cardiac lead extractor and method of use are provided in order to impart a substantial pulling force at the general location of an electrode or distal tip. The extractor device includes generally coaxial elongated components that move relative to each other so as to impart a generally radial, outwardly directed wedging force onto the inside surface of the lead being extracted and near a distal end thereof. In this way, a pulling force can be imparted directly to a location near the distal end of the lead in order to dislodge an overgrown electrode and the like from its implanted location, after which, the entire lead can be removed.

During the several years that cardiac pacing leads, pervenous leads or the like have been in use, important strides have been made toward improving the fixation attributes of the electrode or tip portions of these lead devices. In a typical implantation procedure, an elongated lead is passed through a suitable vein or the like until each tip thereof is advanced to a desired location, typically in the atrium and/or the ventricle of the heart. Accurate location of the tip or electrode is important in order to be assured that the proper amount of contraction current and/or voltage are imparted to the desired area and in order to be assured that the amplitude of the voltage generated by the cardiac contraction or the like is adequately sensed by the cardiac pacer or the like.

Many approaches have been taken in order to maintain the desired location once the lead has been properly positioned thereat. In this regard, numerous means have been provided for substantially secure fixation at the desired location. For example, protuberances such as tines, fins, flanges, ribs and the like have been added to the external surface of the lead in the vicinity of the tip or electrode in order to assist in stabilizing the lead at the desired location by providing extending members which link or stabilize the tip or electrode at the position that provides the desired electrophysiological threshold and amplitude measurements. Another successful means for enhancing proper location and intracardiac fixation that has been successfully implemented over the years is to provide the tip or electrode with a porous, irregular or foraminous surface that is of a size suitable to permit the ingrowth of tissue or villi thereinto from the surrounding implantation location, which ingrowth provides long-term stability to the implanted cardiac pacing lead or the like.

Such enhanced fixation, however, has been found to be a detriment on those occasions when it becomes necessary to remove a securely implanted lead, especially one that had been implanted for a long period of time and with the aid of enhanced fixation devices or surfaces. In this regard, it occasionally becomes necessary to remove a particular cardiac pacing lead, for example if an infection has begun to develop or if the lead had begun to deteriorate for one reason or another.

Heretofore, removal techniques typically have involved pulling on the implanted lead by grasping it at a location that is spaced a substantial distance from the implanted electrode or remote tip, typically by grasping the proximal end portion of the lead and attempting to pull the lead out of the vein or the like through which it had been implanted. Grasping and pulling on the proximal end results in directing pulling forces substantially along the length of the lead, which pulling forces are transmitted through the lead to the implanted electrode or distal tip. When implantation of the tip or electrode has been aided by fixation structures and techniques, an especially substantial resistance to the pulling forces is experienced, thereby placing substantial stress on the lead.

A typical lead has a general construction including a polymeric sheath within which an electrical conductor is mounted. Often, the electrical conductor takes the form of a coil of wire. When a lead such as one having this type of a structure is subjected to pulling forces along its length, the lead can become disassembled. Such undesirable disassembly can include having the polymeric insulating sheath break away from the conductive wire, resulting in a situation where the insulating sheath could be pulled out of the patient while the bare conductor wire coil would remain within the patient. Typically, this situation is avoided by refraining from removing a lead that shows any indication that it is becoming disassembled. If a lead remains intact when the pulling force is exerted on its proximal end, it will be removed, but if the lead begins to break up, often the lead will be capped off and left implanted within the patient, although this is not possible when infection is present.

There is accordingly a need for a device that will remove an implanted lead or the like, even one that may have beem implanted for many years and that has enhanced fixation structures or features. Such a device should ideally effect this removal in an efficient, quick, simple and atraumatic manner, while substantially eliminating the likelihood of lead disassembly and the need to have an inactive lead remain implanted.

These needs and objectives are met by the present invention, which, in its advantageous functional aspects, transmits pulling forces directly to the general location of the electrode or distal tip, rather than having those pulling forces imparted to the proximal end of the lead and along the length of the lead. The invention is directed to an extractor device and its method of use, which device includes means for grasping an interior portion of the lead at a location at or in close proximity to an electrode or distal tip of the lead.

In the illustrated preferred embodiment, the extractor device includes a generally non-elastic, flexible elongated tube having external dimensions which permit its passage into and through the interior longitudinal passageway or lumen of an implanted lead such as a pervenous lead for cardiac pacing. A length of line is coaxially mounted within the lumen of the tube such that the line projects out of both the proximal end and the distal end of the tube, the distal end of the line having a protrusion. When the proximal end of this line is pulled while the tube is held so as to be substantially stationary, the protrusion wedgingly engages the end of the tube and moves into the end portion thereof to thereby radially expand the distal end portion of the tube. Such radially expanded distal end portion of the tube in turn imparts a substantially radially directed outward force onto the interior of the lead at that distal location of the extractor device, which is near an electrode or distal tip of the implanted lead. Thereafter, and while this wedging force is maintained, the proximal end of the extractor device is pulled in order to remove the electrode or distal end and any fixation means associated therewith from the tissue which has grown around and into same. Once this dislodgement is accomplished, the extractor and lead can be pulled as a unit out of the heart and vein, during which procedure the lead is maintained intact and substantially fully assembled.

It is accordingly a general object of the present invention to provide improved means for removing an implanted lead, especially a pervenous cardiac pacing lead.

Another object of the present invention is to provide an improved cardiac lead extractor and method which imparts a pulling force on an implanted lead in the vicinity of its electrode or distal tip that is substantially securely fixed to cardiac tissue.

Another object of the present invention is to provide an improved device and method for extracting a lead by imparting radially outwardly directed forces onto the internal portion of an implanted lead at a location that is at or near the location of an electrode or distal tip thereof that has been implanted with the assistance of fixation devices and/or techniques.

Another object of the present invention is to provide an improved device and method for extracting a pervenous lead from the atrium and/or ventricle of the heart.

Another object of the present invention is to provide an improved means and method for reversing, in a substantially atraumatic, efficient and simple manner, years of lead fixation overgrowth and ingrowth.

Another object of the present invention is an improved device and method which utilize radial wedging for grasping a portion of a lead that is at or near an electrode or distal tip of an implanted pervenous lead or the like.

These and other objects of the present invention will be apparent from the following description of this invention, taken in conjunction with the accompanying drawings, wherein:

FIG. 1 is a schematic illustration of a pervenous lead implanted in the right ventricle of a heart and having an extractor mechanism in accordance with this invention located therewithin;

FIG. 2 is an elevational view, partially broken away, of a preferred extractor assembly in accordance with this invention;

FIG. 3 is an elevational view of an alternative embodiment of the distal end portion of an extractor assembly in accordance with this invention;

FIG. 4 is an elevational view, partially broken away, of an extractor assembly mounted within a typical pervenous cardiac pacing lead;

FIG. 5 is a partial longitudinal sectional view, partially broken away, of the assembly illustrated in FIG. 4; and FIG. 5 is a partial longitudinal sectional view, partially broken away, of the assembly of FIG. 4 and illustrating the assembly in its wedging and grasping condition.

A cardiac pacing lead, generally designated as 21 in FIG. 1, is illustrated such that an implanted electrode 22 (FIG. 4) is fixed at its most distal tip by tissue and/or villi 23 in the right ventricle 24 of the illustrated heart 25. It is to be understood that the implanted condition generally illustrated in the drawing includes having a substantial length of the cardiac pacing lead 21 implanted within an appropriate vein (not shown) of the patient, while the proximal end 26 of the lead 21 is accessible for connection to a pacemaker in accordance with generally well-known structures and procedures. As shown in FIG. 4, fixation means such as the illustrated tines 27 and/or the illustrated porous surface 28 of the electrode 22 may be provided at the distal end portion 29 of the electrode 22.

A lead extractor assembly, generally designated as 31 in FIG. 2, includes an elongated tubular member 32 within which is slidably mounted an elongated length of line 33. As is evident from FIGS. 1, 4, 5 and 6, the lead extractor assembly 31 has an outer diameter or peripheral size that permits its sliding passage into and through a longitudinal lumen 34 of the cardiac pacing lead 21. Additionally, the elongated line member is coaxially and slidably mounted into and through a lumen 35 through the elongated tubular member 32.

The distal end of the elongated line member 33 includes a protrusion member 36, such as the generally spherical ball that is illustrated in FIGS. 2, 5 and 6. Protrusion member 36 may assume various other shapes, such as the generally conical member 36a shown in FIG. 3. Protrusion member 36 should have a structure whereby same has a maximum radially directed diameter that is less than the diameter of the longitudinal lumen 34 of the lead 21 and that is greater than the diameter of the lumen 35 of the elongated tubular member 32. Most advantageously, the protrusion member 36 includes a generally tapering proximal surface which provides a structure in the nature of a radially disposed inclined plane for providing a generally radial wedging surface. In the embodiment illustrated in FIG. 2, the proximal generally tapering surface takes the form of a spherical section 37 between the distal end of the elongated line member 33 and a gripping circumference 38 thereof that is radially directed with respect to the axis of the elongated line member 33. In the embodiment illustrated in FIG. 3, the proximal tapering surface takes the form of a conical section 37a positioned between the distal end of the elongated line member 33 and a gripping circumference 38a at the proximal edge of a generally annular surface 39.

When proximal end portion 40 of the elongated line member 33 is pulled, for example by grasping a handle 46, while the elongated tubular member 32 is maintained generally stationary, the protrusion member engages internal distal edge 41 of the elongated tubular member 32. If pulling is continued with adequate force, the proximal tapered surface 37, 37a imparts a force on the distal edge 41, which force has components that are in both a radial outward direction and an axial direction toward the proximal end. This force continues until the gripping circumference or surface 38, 38a engages the internal distal edge 41 of the tube 32, whereby the protrusion member 36, 36a moves inwardly of the elongated tubular member 32 to a location that is generally illustrated in FIG. 6. Inasmuch as the gripping circumference or surface 38, 38a of the protrusion member 36, 36a is larger than the distal edge 41 and the lumen 35 at the distal portion of the elongated tubular member 32, such pulling on the proximal end portion 40 of the elongated line member 33 forms a flared distal end section 42 (FIG. 6) of the elongated tubular member 32.

With more particular reference to the gripping surface 38, 38a of the protrusion 36, 36a, its maximum radially directed dimension is predetermined to also take into consideration the wall thickness of the elongated tubular member 32 at and near the distal edge 41. More particularly, this maximum radially directed dimension, for example, its diameter, of the gripping surface 38, 38a is slightly greater than the difference between the inside diameter of the longitudinal lumen 34 of the cardiac pacing lead 21 at its distal end portion and twice the wall thickness of the elongated tubular member 32. By virtue of this predetermined dimensional relationship, the formed flared distal end section 42 of the elongated tubular member 32 will, by virtue of a wedging-type of action, grippingly engage and possibly radially expand the lumen 34 of the cardiac pacing lead 21.

In a typical cardiac pacing lead 21 of the type illustrated in the drawings, this longitudinal lumen 34 is the inside surface of a coiled elctrical conductor 43 (FIGS. 5 and 6) of the cardiac pacing lead 21. Illustrated cardiac pacing lead 21 also includes a polymeric insulator sheath 44 that provides an insulating covering for the coiled electrical conductor 43. When a coiled electrical conductor 43 is involved, such provides an opportunity for enhancing the wedging action by springing engagement between the flared distal end section 42 and a turn 47 of the coiled conductor 43. Such springing engagement occurs when one or more turns 47 are radially expanded by the flared end section 42, and the thus expanded turn(s) 47 will impart an inwardly biased spring-like force onto the flared end section 42.

Formation of the flared distal end section 42 is preferably facilitated by providing one or more longitudinal slots 45 opening into the distal edge 41 of the elongated tubular member 32. Longitudinal slot(s) 45 substantially reduce the amount of pulling force needed to wedgingly expand the distal edge 41, while also ensuring that this pulling force will effect an expansion of the distal edge 41 and formation of the flared distal end section 42. Longitudinal slot(s) 45 are particularly advantageous and quite important to te lead extractor assembly 31 when the elongated tubular member 32 is made of a material that does not readily tear or stretch, such as stainless steel, which is the preferrd material for the elongated tubular member 32. Elongated tubular member 32 also may be made of materials such as high-strength polymers, for example polyetherimides, polyesters, polycarbonates or the like.

Slots 45 are very desirable. In this regard, the formation of slots 45 through an extremely small member such as the tube 32 typically requires relatively sophisticated technology, especially when the tube 32 is made of a high-strength material such as stainless steel. Suitable technology for slitting or forming slots 45 includes laser severance techniques, electrical discharge milling, and wire electrical discharge milling. For example, these techniques are capable of forming a slot 45 showing a width of 0.002 inch within a tube 32 having an outside diameter of 0.024 inch.

Elongated tubular member 32 has a length such that it projects beyond the proximal end 26 of the lead 21 when the lead extractor assembly 31 is fully inserted into the lead 21. The elongated line member 33, which may be a monofilament or stranded and made of a metal wire such as stainless steel or a thread of a natural or synthetic material, has a length that is greater than the length of the elongated tubular member 32 so that the proximal end portion 40 thereof can be readily grasped.

In use, the lead extractor assembly 31 is inserted into and through an implanted cardiac pacing lead 21 as generally illustrated in FIG. 1, the lead extractor assembly 31 being sufficiently pliant to follow the curved pathway of the implanted lead 21. The lead extractor assembly 31 is advanced until the protrusion member 36, 36a generally abuts the proximal end of the implanted electrode 22. Usually, insertion of the extractor assembly 31 will be assisted by fluoroscopy. If desired the protrusion member 36, 36a could be made of a material such as platinum that is especially visible under fluoroscopy.

Next, the proximal end of portion 48 the elongated tubular member 32 is grasped so as to prevent any substantial movement thereof, and the proximal end portion 40 of the elongated line member 33 is pulled, thereby withdrawing the protrusion member 36, 36a into the distal end portion of the elongated tubular member 32 in order to form the flared distal end section 42 thereof and to wedge same into tight frictional engagement with the inside surface of the distal portion of the cardiac pacing lead 21. Thereafter, a pulling force is exerted on the proximal end portion 48 of the elongated tubular member 32, which pulling force is transmitted along the length of the lead extractor assembly 31 and to the flared distal end section 42, which in turn results in pulling the distal end of the cardiac pacing lead in order to dislodge same and electrode 22 from the fixation tissue and villi 23 while avoiding or substantially minimizing the application of any stress or strain forces on the conductor 43 or its insulator sheath 44. Thereafter, the entire lead assembly 21 and the extractor assembly 31 mounted therewithin are removed as a unit through the vein or the like of the patient, and the lead assembly 21 and extractor assembly 31 can be discarded.

It is to be appreciated that this invention can be embodied in various forms and therefore is to be construed and limited only by the scope of the appended claims.

I claim:

1. An extractor assembly for removing an implanted cardiac pacing lead assembly and the like which has an elongated shaft that has a distally located remote electrode or the like implanted within a cardiac passageway, comprising:

an elongated tubular member that is pliable and that has an outer diameter which is less than the diameter of a longitudinal lumen through the cardiac pacing lead, said elongated tubular member having a length that is at least as long as the length of the elongated lead assembly shaft, said elongated tubular member having an lumen throughout its length, and wherein the distal end of said member defnes means for engaging the longitudinal lumen of said lead;

an elongated line member that is generally coaxial with and slidably mounted within said lumen of the elongated tubular member, said elongated line member having an outer diameter that is less than the diameter of the elongated tubular member lumen, said elongated line member having a length that is longer than said length of the elongated tubular member; and protrusion means at the distal end of said elongated line member, said protrusion means having a maximum radially directed dimension that is less than a corresponding dimension of the longitudinal lumen through the cardiac pacing lead assembly and that is greater than a corresponding dimension of said lumen through the elongated tubular member for effecting the engagement of said member to said lead.

2. The extractor assembly according to claim 1, wherein said maximum radially directed dimension of the protrusion means is also greater than the difference between said dimension of the lead assembly lumen and twice the wall thickness of said elongated tubular member.

3. The extractor assembly according to claim 1, wherein said protrusion means and a distal end portion of the elongated tubular member combine to form means for effecting the radially outwardly directed wedging forces directly onto a distal end portion of said longitudinal lumen of the cardiac pacing lead.

4. The extractor assembly according to claim 3, wherein said means for effecting wedging forces includes means for axially moving said protrusion means in a proximal direction, said axial moving means including said elongated line member.

5. The extractor assembly according to claim 3, wherein said means for effecting wedging forces includes means for forming a distal end portion of elongated tubular member into a flared distal end section.

6. The extractor assembly according to claim 5, wherein the cardiac pacing lead assembly includes a coiled conductor having said lumen of the cardiac pacing lead, and said flared distal end section springingly engages at least one turn of the coiled conductor.

7. The extractor assembly according to claim 1, wherein said protrusion means includes a generally tapering proximal surface generally between the distal end of the elongated line member and a gripping surface having said maximum radially directed dimension.

8. The extractor assembly according to claim 7, wherein said generally tapering proximal surface is a spherical section.

9. The extractor assembly according to claim 7, wherein said generally tapering proximal surface is a conical section.

10. The extractor assembly according to claim 1, wherein said elongated tubular member includes at least one longitudinal slot opening into distal edge of the elongated tubular member.

11. A method for extracting an implanted cardiac pacing lead assembly and the like which has an elongated lead shaft that has a distally located remote electrode implanted within a cardiac passageway, comprising the steps of:

providing an extractor assembly having a pliable elongated tubular member and an elongated line member slidably mounted coaxially within a lumen thereof and extending proximally of the elongated tubular member, the elongated line member also protruding distally of the elongated tubular member and including distal protrusion means;

inserting the extractor assembly, protrusion means first, into and through a lumen of an implanted cardiac pacing lead assembly and the like until the protrusion means generally engages a distal end of the cardiac pacing lead lumen;

holding the elongated tubular member generally stationary while manipulating the proximal end of the elongated line member in order to impart a generally radially directed wedging force onto the generally distal end of the cardiac pacing lead lumen;

pulling the extractor assembly in a proximal direction to thereby transmit a pulling force directly onto the distal end portion of the cardiac pacing lead to thereby dislodge the implanted distal tip; and thereafter withdrawing the cardiac pacing lead assembly and lead extractor assembly from the patient.

12. The extracting method according to claim 11, wherein said holding and manipulating step includes pulling the proximal end of the elongated line member in a proximal direction and sliding the elongated line member within the elongated tubular member in order to move the protrusion means into a distal end portion of the elongated tubular member and to form a flair in the distal end portion.

13. The extracting method according to claim 11, wherein said providing step includes sizing the protrusion means to have a maximum radially directed dimension that is less than a corresponding dimension of the lumen of the implanted cardiac pacing lead assembly and that is greater than a corresponding dimension of the lumen of the elongated tubular member.

14. The extracting method according to claim 13, wherein the maximum radially directed dimension of said sizing step is also greater than the difference between said dimension of the lead assembly and twice the wall thickness of the elongated tubular member.

15. The extracting method according to claim 11, wherein said holding and manipulating step includes engaging a turn of a conductor coil of the lead assembly whereby said turn springingly contacts a distal end of the elongated tubular member.

16. The extracting method according to claim 11, wherein said providing step includes forming at least one slot opening into a distal edge of the elongated tubular member.

17. The extracting method according to claim 11, wherein said inserting step includes sliding the extractor assembly until the same enters a heart atrium or ventricle while being within the cardiac pacing lead assembly.

* * * * *